(12) United States Patent
Clarke et al.

(10) Patent No.: US 8,263,171 B2
(45) Date of Patent: Sep. 11, 2012

(54) METHODS FOR MAKING DRUG-ELUTING MEDICAL DEVICES

(75) Inventors: John T. Clarke, Claregalway (IE); Timothy O'Connor, Claregalway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 934 days.

(21) Appl. No.: 12/170,889

(22) Filed: Jul. 10, 2008

(65) Prior Publication Data

US 2009/0017188 A1 Jan. 15, 2009

Related U.S. Application Data

(60) Provisional application No. 60/949,640, filed on Jul. 13, 2007.

(51) Int. Cl.
*A61L 27/54* (2006.01)

(52) U.S. Cl. ...... 427/2.25; 427/2.1; 427/2.14; 427/2.24; 427/258; 623/1.15; 623/1.4; 623/1.42; 623/1.46

(58) Field of Classification Search ............ 427/2.1, 427/2.14, 2.24, 2.25, 258; 623/1.15, 1.4, 623/1.42, 1.46
See application file for complete search history.

(56) References Cited

U.S. PATENT DOCUMENTS

| 6,585,765 | B1 | 7/2003 | Hossainy et al. |
| 2004/0088038 | A1* | 5/2004 | Dehnad et al. ............... 623/1.15 |
| 2009/0123517 | A1* | 5/2009 | Flanagan et al. ............. 424/423 |

FOREIGN PATENT DOCUMENTS

| WO | 2008/034007 A | 3/2008 |
| WO | 2008/057991 A | 5/2008 |

OTHER PUBLICATIONS

International Preliminary Report on Patentability and Written Opinion of the International Searching Authority for PCT/US2008/069626, dated Jan. 28, 2010.
International Search Report and Written Opinion of the International Searching Authority for PCT/US2008/069626, dated Dec. 2, 2008.

* cited by examiner

*Primary Examiner* — Brian P Mruk
(74) *Attorney, Agent, or Firm* — Kenyon & Kenyon LLP

(57) ABSTRACT

The present invention is directed to medical implants that are configured to controllably release therapeutic agent to a target site of a patient and methods of making these implants. Embodiments of the present invention may include a method comprising the steps of providing a tube having a wall with inner and outer surfaces and defining a passageway, forming an opening through the wall of the tube, applying a porous coating layer to at least one of the inner and outer surfaces of the tube, and loading a therapeutic agent solution into the passageway so that therapeutic agent passes through the opening and into the porous coating layer. The method may also include removing portions of the tube to form the implantable medical device, which may be a stent.

18 Claims, 4 Drawing Sheets

Step 500
Providing Tubing Having a Wall With Inner and Outer Surfaces

Step 510
Forming an Opening Through the Wall of the Tubing

Step 520
Applying a Porous Coating Layer to at least one of the Inner and Outer Surfaces of the Tubing

Step 530
Loading a Therapeutic Agent Solution Through the Opening in the Wall and Into the Porous Coating Layer

Step 540
Removing Portions of the Tubing to Form an Implantable Medical Device

FIG.5

METHODS FOR MAKING DRUG-ELUTING MEDICAL DEVICES

CROSS REFERENCE TO RELATED APPLICATION

The present application claims priority to U.S. provisional application Ser. No. 60/949,640 filed Jul. 13, 2007, the disclosure of which is incorporated herein by reference in its entirety.

TECHNICAL FIELD

The present invention generally relates to implantable drug-eluting medical devices and methods of making those devices.

BACKGROUND

The positioning and deployment of implantable medical devices within a target site of a patient are common, often repeated, procedures of contemporary medicine. These devices, which may be implantable stents as well as other devices, may be deployed for short or sustained periods of time and may be used for many medicinal purposes. These can include the reinforcement of recently re-enlarged lumens, the replacement of ruptured vessels, and the treatment of disease, such as vascular disease, through the delivery of therapeutic agent.

Coating may be applied to surfaces of implantable medical devices to transport therapeutic agent to a target site and to release it at the target site. In certain systems the therapeutic agent is released immediately upon reaching the target site. This burst release may not be favored in certain circumstances as a large amount of the therapeutic agent may be wasted as it is transported away by bodily fluids before it can be absorbed by the targeted area. Likewise, if large amounts of the therapeutic agent are released immediately upon deployment, less therapeutic agent will remain for sustained release of lower dosages over time.

BRIEF DESCRIPTION

The present invention is directed to medical implants that are configured to controllably release therapeutic agent to a target site of a patient and methods of making these implants. For example, embodiments of the present invention may include a method of making a implantable medical implant, such as a stent, comprising the steps of providing a tube having a wall with inner and outer surfaces and defining a passageway, forming one or more opening(s) through the wall of the tube, applying a porous coating layer to at least one of the inner and outer surfaces of the tube, and loading a therapeutic agent solution through the opening(s) and into the porous coating layer. The method may also include removing portions of the tube to form a stent.

Embodiments of the present invention may also include a method of making a implantable medical implant, such as a stent, comprising the steps of providing a tube having a wall with inner and outer surfaces and defining a passageway, forming one or more opening(s) through the wall of the tube, applying one or more porous coating layers to the outer surface of the tube, and loading a therapeutic agent solution through the opening(s) and into the porous coating layer(s). The one or more porous coating layers may be a plurality of porous coating layers including an innermost layer having a relatively large pore size and one or more successive layers which incrementally decrease in pore size so that an outermost layer has the smallest pore size. The method may also include removing portions of the tube to form a stent.

The invention may be embodied by numerous other devices and methods. The description provided herein, when taken in conjunction with the annexed drawings, discloses examples of the invention. Other embodiments, which incorporate some or all steps as taught herein, are also possible.

BRIEF DESCRIPTION OF THE DRAWINGS

Referring to the drawings, which form a part of this disclosure:

FIG. 1a shows an end view of a parent tubing section having a plurality of porous coatings as may be employed in accordance with embodiments of the present invention and FIG. 1b shows a cross-sectional view taken along the line 1b-1b in FIG. 1a;

FIG. 5 is a flow chart of method steps that may be employed in accordance with embodiments of the present invention.

DETAILED DESCRIPTION

The present invention generally relates to implantable medical devices such as stents that deliver therapeutic agent to target sites of a body. This therapeutic agent may be carried such that it can be released by the implant for sustained periods of time at the target site. In embodiments of the present invention the therapeutic agent may be loaded into pores that meter the release of the therapeutic agent. For example, embodiments of the present invention may include a coating or coatings having voids and interstices of various sizes and shapes with dimensions in the nanometer and micrometer range. These voids and interstices may be homogenous in size and non-homogeneous in size as well. Likewise, the coating(s) may also be comprised of two or more porous regions with different porosities and pore sizes. In each example, the same or different therapeutic agents may be loaded into each region.

In some embodiments, the therapeutic agent may be transported, released or both without the use of additional carrier polymers. By reducing or eliminating the use of polymers the potential for inflammatory reactions associated with the use of polymers may be reduced or eliminated.

Figure 1A:
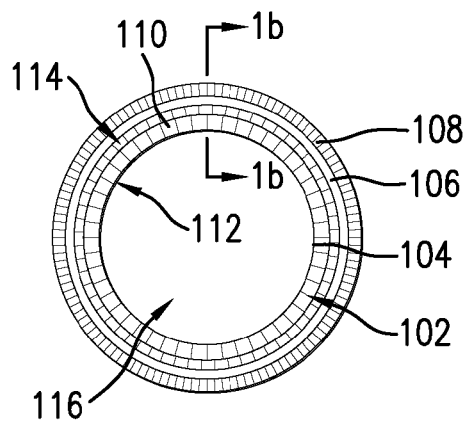
Figure 1B:
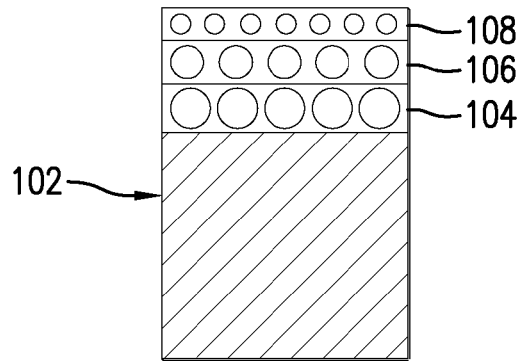

Referring initially to FIGS. 1a-b, end and cross-sectional views of a parent tubing section 102 are shown having a plurality of porous coatings 104, 106, 108 as may be employed in accordance with embodiments of the invention. As seen in FIG. 1a, the parent tubing section 102 may be tubular shaped and may have a wall 110 with inner and outer surfaces 112, 114. The wall may define a passageway 116. The parent tubing section 102 may be made from any suitable material. For example, suitable materials include, but are not limited to, stainless steel, CoCr, NiTi, polymers, ceramics, and platinum enriched stainless steel.

Figure 2A:
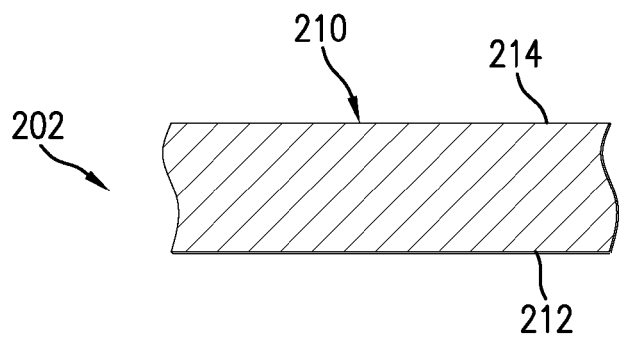
FIG. 2a shows a wall of a section of parent tubing.
Figure 2B:
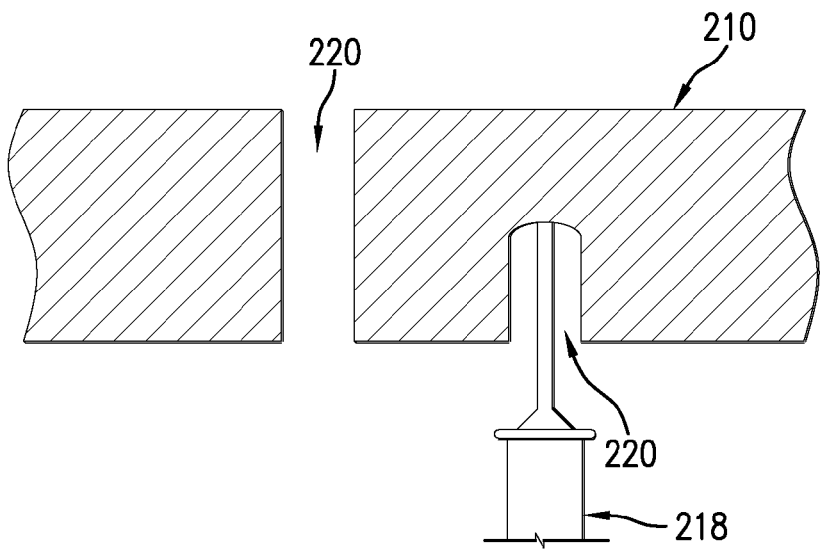
FIG. 2b shows a system for forming an opening through the wall as may be employed in accordance with embodiments of the present invention.

FIG. 2a shows a portion of a wall 210 of parent tubing section 202, similar to the wall 110. The walls has inner and outer surfaces 212, 214. FIG. 2b shows a laser drilling system 218 for pre-forming therapeutic agent loading holes or openings 220 in the parent tubing wall 210. Any suitable system may be used for pre-forming the holes 220. For example, electron beam drills and laser drilling systems are suitable. Any number of holes 220 may be formed in the wall 210. In the example, the holes 220 may be formed in portions of the parent tubing section that may be cut away later during laser cutting of the medical device from the parent tubing section (e.g, FIG. 4a). For example, in the case of a stent, this may be the area between the struts.

Figure 3A:
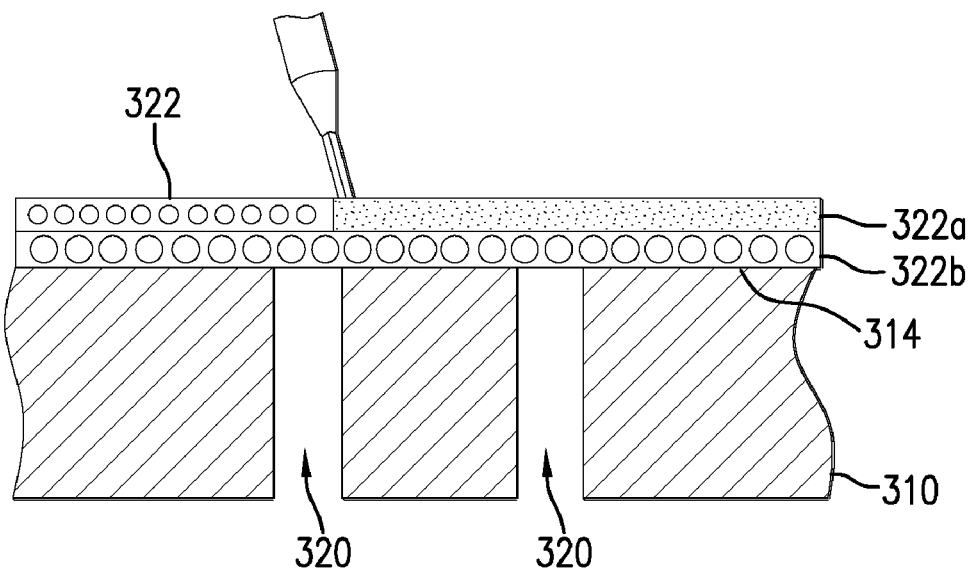
FIG. 3a shows a system for applying a porous coating layer to the parent tubing section.

As seen in FIG. 3a, a porous coating 322 having a plurality of layers 322a, 322b may be applied to the outer surface 314 of the wall 310. In the example the porous coating 322 is applied following the formation of the holes 320; however, it is contemplated by embodiments of the invention that the porous coating 322 may be applied prior to drilling of the holes 320.

The porous coating 322 may be used to store and regulate the release of therapeutic agent. The porous coatings 322 can be created by several methods, including vapor deposition processes, CVD, PVD, plasma deposition, electroplating, sintering, sputtering or other methods known in the art. Porous medical devices or layers of porous material deposited on medical devices may be made from a powdered material such as powdered metal, ceramics, bio-ceramics, and/or polymers. Suitable materials typically should not produce toxic reactions or act as carcinogens.

Since the rate of drug elution from a porous region may be determined by the pore size of the voids and chambers, the medical devices of the present invention may also be prepared with different pore sizes and may be prepared having a range of porosities allowing for the production of medical devices with differing therapeutic agent delivery characteristics. For example, to facilitate the modulation of therapeutic release, the chambers and voids may be built up from a plurality of layers having different pore densities.

In the example of FIG. 3a, an elution layer 322a, with the smallest pore size, can be provided as the outermost layer to control drug release. Smaller size pores may enable sustained therapeutic agent delivery over a reasonable timescale, for example, about three months. Likewise, a reservoir layer 322b, with the largest pore size, can be provided as the innermost layer, which is closest to the parent tubing section. The larger pores of the reservoir layer 322b may act as reservoirs for therapeutic agent. If additional layers are added, the pore size of the outer layers can be made so that there is an incremental decrease in pore size at each successive layer with the outermost layer having the smallest pore size (e.g., the outermost layer may have pores in the nanometer range while the innermost layer may have pores in the micrometer range).

Figure 3B:
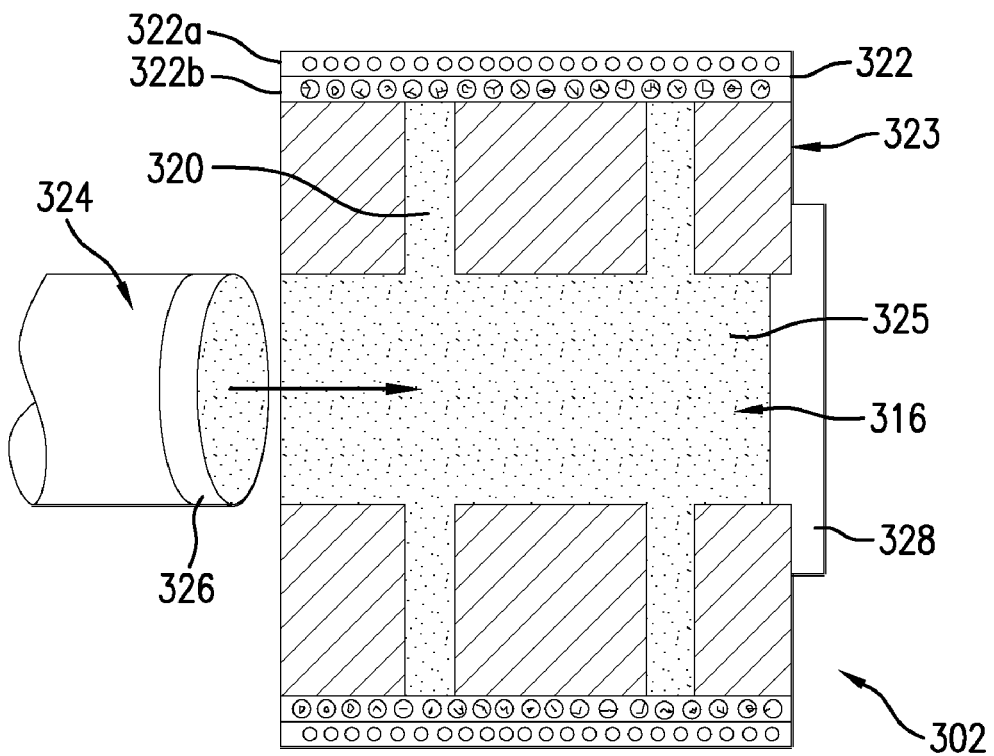
FIG. 3b shows a system for loading the coating with therapeutic agent as may be employed in accordance with embodiments of the present invention.

FIG. 3b shows an injection system 324 for loading therapeutic agent 325 into the porous coating layers 322a, 322b. In the example, a pressurized supply of a therapeutic agent and solvent solution may be applied to the passageway 316 of the medical device 302 from a injection source 326. In the example, one end of the passageway may be sealed with a sealing member 328. The therapeutic agent and solvent solution passes through the holes 320 to fill the reservoir layer 322b and then the elution layer 322a. For instance, in FIG. 3b, the large reservoir pores of the reservoir layer 322b may be filled with therapeutic agent 325. The solvent may be later evaporated off using conventional solvent evaporation methods. For example, a vacuum chamber may be used for evaporating solvent from the medical device following loading (the vacuum chamber may also be used for removing air from the pores prior to loading). Over time, such as in vivo, the therapeutic agent 325 may diffuse from the reservoir layer 322b to the outer pores of the elution layer 322a and then exit to a target site of a patient. As the pores of the elution layer 322a may be smaller, they may limit the escape of therapeutic agent 325 over a desired time period so that the elution rate may be controlled.

Figure 4A:
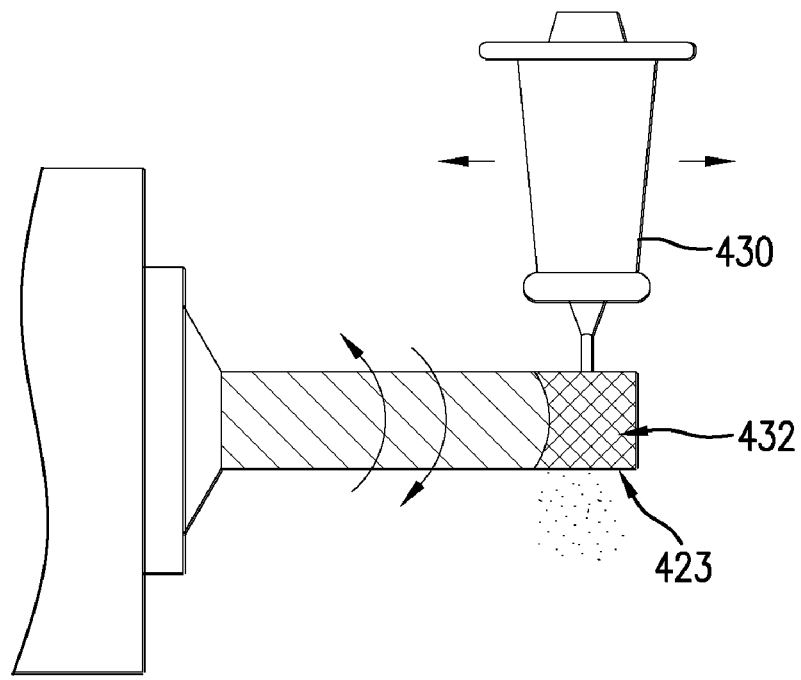
FIGS. 4a-b show systems for cutting and polishing an implantable medical device as may be employed in accordance with embodiments of the present invention.
Figure 4B:
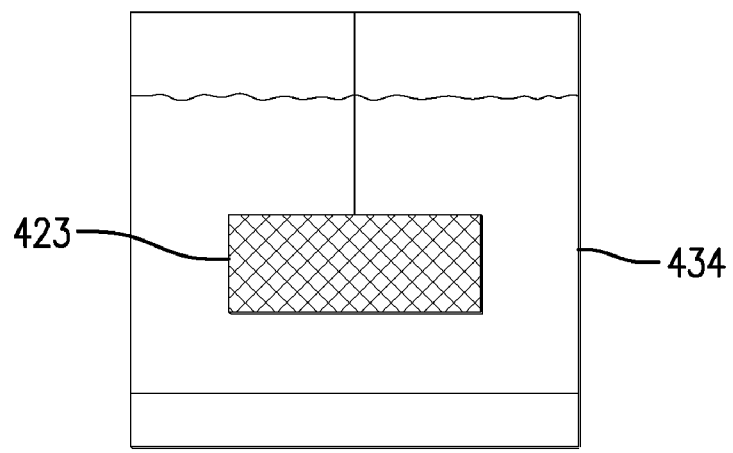

FIGS. 4a-b show systems for cutting and polishing the implantable medical device as may be employed in accordance with embodiments of the present invention. The illustrated device may be a stent or any other suitable device.

FIG. 4a shows the medical device being cut from the parent tubing section having a porous coating in accordance with embodiments of the present invention. FIG. 4a shows a conventional laser 430 cutting away waste metal, thus leaving the desired support structure 432 of the medical device 423 intact. For example, the sections that are cut away to form the support structure 432 of the medical device 423 may be the sections containing the loading holes 220, 320. Thus, when the device is fully manufactured, the holes 220, 320 no longer exist. Alternatively, sections containing loading holes 220, 320 may remain.

The cutting system may include computer controlled machinery components and hardware/software components for precision cutting of one or more medical devices during the manufacturing process.

FIG. 4b shows the medical device 423 being polished in accordance with embodiments of the present invention. In this example, the medical device 423 is being electro-polished in a electrochemical bath 434; however, any suitable polishing techniques may be used for removing excess material and inconsistencies, such as burrs and edges, from surfaces of the medical device 423.

FIG. 5 shows a flow chart including method steps that may be employed with embodiments of the present invention for making an implantable medical device for controllably releasing a therapeutic agent. In the example of FIG. 5, step 500 may include providing tubing having a wall with inner and outer surfaces. Step 510 may include forming an opening through the wall of the tubing. Step 520 may include applying a porous coating layer to at least one of the inner and outer surfaces of the tubing. Step 530 may include loading therapeutic agent through the opening in the wall and into the porous coating layer. Step 540 may include removing portions of the tubing to form an implantable medical device, such as a stent.

In other embodiments, not shown, the sequence of steps may be reordered and steps may be added or removed. The steps may also be modified.

Although in some embodiments a stent is shown, any implantable medical device may be used or made in accordance with embodiments of the present invention. For instance, defibrillators, filters, grafts, catheters, and/or any implantable devices for systemic release of drugs may be used. The implantable medical devices may be self-expanding, mechanically expandable, or of a hybrid configuration which exhibits both self-expanding and mechanically expandable characteristics. The implantable medical devices may be made in a wide variety of designs and configurations, and may be made from a variety of materials including metals, ceramics, bio-ceramics, and/or polymers.

While various embodiments have been described, other embodiments are plausible. It should be understood that the foregoing descriptions of various examples of the implantable medical devices having porous structures and methods for making and loading the same are not intended to be limiting, and any number of modifications, combinations, and alternatives of the examples may be employed to facilitate the effectiveness of delivering therapeutic agent from the porous structure to a target site of a patient.

The term "therapeutic agent" as used herein includes one or more "therapeutic agents" or "drugs." The terms "therapeutic agents" or "drugs" can be used interchangeably herein and include pharmaceutically active compounds, nucleic acids with and without carrier vectors such as lipids, compacting agents (such as histones), viruses (such as adenovirus, adenoassociated virus, retrovirus, lentivirus and (α-virus), polymers, hyaluronic acid, proteins, cells and the like, with or without targeting sequences.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, CDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; anti-proliferative agents such as enoxaprin, angiopeptin, rapamycin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMPs"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMPs are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

The examples described herein are merely illustrative, as numerous other embodiments may be implemented without departing from the spirit and scope of the exemplary embodiments of the present invention. Moreover, while certain features of the invention may be shown on only certain embodiments or configurations, these features may be exchanged, added, and removed from and between the various embodiments or configurations while remaining within the scope of the invention. Likewise, methods described and disclosed may also be performed in various sequences, with some or all of the disclosed steps being performed in a different order than described while still remaining within the spirit and scope of the present invention.

What is claimed is:

1. A method of making an implantable medical device for controllably releasing a therapeutic agent, the method comprising:
   providing a tube having a wall with inner and outer surfaces and defining a passageway;
   forming an opening through the wall of the tube;
   applying a porous coating layer to at least one of the inner and outer surfaces of the tube so as to cover the opening following formation of the opening;
   loading a therapeutic agent through the opening and into the porous coating layer; and
   removing portions of the tube to form the implantable medical device after the porous coating layer is applied to the tube,
   wherein the therapeutic agent is loaded from the inner surface of the wall of the tube, through the opening to the outer surface of the wall of the tube, and into the porous coating layer.

2. The method of claim 1 further comprising applying a plurality of porous coating layers.

3. The method of claim 2 wherein the plurality of porous coating layers have different pore sizes.

4. The method of claim 3 wherein the porous coating layer with the largest average pore size is the innermost layer.

5. The method of claim 3 wherein the porous coating layer with the smallest average pore size is the outermost layer.

6. The method of claim 1 further comprising forming a plurality of openings.

7. The method of claim 1 wherein the implantable medical device is a stent.

8. The method of claim 1 wherein the therapeutic agent is delivered in a solution including a solvent.

9. The method of claim 8 further comprising evaporating the solvent from the porous coating layer.

10. A method of making a stent for controllably releasing a therapeutic agent, the method comprising:
    providing a tube having a wall with inner and outer surfaces and defining a passageway;
    forming an opening through the wall of the tube;
    applying a porous coating layer to the outer surface of the tube so as to cover the opening following formation of the opening;
    loading a therapeutic agent through the opening and into the porous coating layer; and
    removing portions of the tube to form the stent after the porous coating layer is applied to the tube,
    wherein the therapeutic agent is loaded from the inner surface of the wall of the tube, through the opening to the outer surface of the wall of the tube, and into the porous coating layer.

11. The method of claim 10 further comprising applying a plurality of porous coating layers.

12. The method of claim 11 wherein the plurality of porous coating layers have different pore sizes.

13. The method of claim 12 wherein the porous coating layer with the largest average pore size is the innermost layer.

14. The method of claim 12 wherein the porous coating layer with the smallest average pore size is the outermost layer.

15. The method of claim 10 further comprising forming a plurality of openings.

16. A method of making a stent for controllably releasing a therapeutic agent, the method comprising:
    providing a tube having a wall with inner and outer surfaces and defining a passageway;
    forming an opening through the wall of the tube;
    applying a plurality of porous coating layers to the outer surface of the tube so as to cover the opening following formation of the opening, wherein an innermost layer has the largest pore size and successive layers incrementally decrease in pore size so that an outermost layer has the smallest pore size;
    loading therapeutic agent solution into the passageway so that therapeutic agent passes through the opening and into the porous coating layers; and
    removing portions of the tube to form the stent after the porous coating layers are applied to the tube,
    wherein the therapeutic agent is loaded from the inner surface of the wall of the tube, through the opening to the outer surface of the wall of the tube, and into the porous coating layers.

17. The method of claim 16 further comprising forming a plurality of openings.

18. The method of claim 16 wherein portions of the tube are removed with a laser.

* * * * *